(12) United States Patent
Ono

(10) Patent No.: US 11,003,633 B2
(45) Date of Patent: May 11, 2021

(54) ANALYSIS INFORMATION MANAGEMENT SYSTEM

(71) Applicant: SHIMADZU CORPORATION, Kyoto (JP)

(72) Inventor: Koji Ono, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 193 days.

(21) Appl. No.: 16/060,520

(22) PCT Filed: Dec. 9, 2015

(86) PCT No.: PCT/JP2015/084498
§ 371 (c)(1),
(2) Date: Jun. 8, 2018

(87) PCT Pub. No.: WO2017/098599
PCT Pub. Date: Jun. 15, 2017

(65) Prior Publication Data
US 2019/0050422 A1 Feb. 14, 2019

(51) Int. Cl.
*G06F 16/00* (2019.01)
*G06F 16/18* (2019.01)
(Continued)

(52) U.S. Cl.
CPC ......... *G06F 16/1805* (2019.01); *G01N 30/86* (2013.01); *G06F 16/13* (2019.01); *G06F 16/23* (2019.01); *G06Q 50/00* (2013.01)

(58) Field of Classification Search
CPC ........ G01N 30/86; G06Q 50/00; G06Q 10/06; G06F 16/1805; G06F 16/13; G06F 16/23;
(Continued)

(56) References Cited

U.S. PATENT DOCUMENTS 6,078,924 A * 6/2000 Ainsbury ............... G06F 16/951
6,671,818 B1 * 12/2003 Mikurak ................ G06Q 10/06
714/4.21
(Continued)

FOREIGN PATENT DOCUMENTS

JP 2005-156473 A 6/2005
JP 2015-152350 A * 8/2015

OTHER PUBLICATIONS

"Class-Agent Ver. 2 Nettowaaku Taiou Bunseki Deeta Kanri Tsuuru (Class-Agent Ver. 2, Network-Compatible Analysis Data Management Tool)", [online], Shimadzu Corporation, [accessed on Dec. 4, 2017], the Internet.
(Continued)

*Primary Examiner* — Shiow-Jy Fan
(74) *Attorney, Agent, or Firm* — Sughrue Mion, PLLC

(57) ABSTRACT

An analysis data collector stores data acquired with an analytical instrument in a file to which a data ID has been given, and registers the file in a database. A log information collector registers, in the database, log information which shows various operations on each analytical instrument or client terminal, state of the device or the like. After data files are selected, a command to create an audit trail is issued, whereupon an audit trail information extractor collects information corresponding to those data files. The audit trail information extractor extracts each piece of log information containing the data ID and pieces of log information which contain the device ID and user ID and were obtained within a time range from login to logout including the date and time of registration. An audit trail creator creates an audit trail by organizing the log information in time-series order, and registers it.

6 Claims, 6 Drawing Sheets

(51) Int. Cl.
*G06Q 50/00* (2012.01)
*G01N 30/86* (2006.01)
*G06F 16/23* (2019.01)
*G06F 16/13* (2019.01)

(58) Field of Classification Search
CPC .......... G06F 16/93; G06F 16/34; G06F 16/16; G06F 16/9038
See application file for complete search history.

(56) References Cited

U.S. PATENT DOCUMENTS

| | | | |
|---|---|---|---|
| 2002/0193966 A1 | 12/2002 | Buote et al. | |
| 2003/0120593 A1* | 6/2003 | Bansal | G06Q 20/10 705/39 |
| 2008/0120129 A1* | 5/2008 | Seubert | G06Q 10/06 705/35 |
| 2009/0254572 A1* | 10/2009 | Redlich | G06Q 10/06 |
| 2011/0010720 A1* | 1/2011 | Smith | G06F 21/00 718/102 |
| 2014/0249857 A1* | 9/2014 | Moore | G06F 19/00 705/3 |

OTHER PUBLICATIONS

"FDA 21 CFR Part 11 Taiou Sofutouea WingSALD bio (WingSALD bio: A software in compliance with FDA 21 CFR Part 11)", [online], Shimadzu Corporation, [accessed on Dec. 4, 2017], the Internet.
International Search Report for PCT/JP2015/084498 dated Feb. 9, 2016 (PCT/ISA/210).
Written Opinion PCT/JP2015/084498 dated Feb. 9, 2016 (PCT/ISA/237).
Communication dated May 13, 2020, from the European Patent Office in European Application No. 15910215.1.
R.D. Mcdowall et al., "The Ideal Chromatography Data System for a Regulated Laboratory, Part II: System Architecture Requirements", LCGC North America, Oct. 2015, vol. 33, No. 10, pp. 782-785 (4 pages total).
"Analytical Data System LabSolutions", Nov. 20, 2014, Retrieved from the Internet: URL:https://www.ssi.shimadzu.com/sites/ssi.shimadzu.com/files/Products/literature/cds/C191-E016.pdf, pp. 1-20 (20 pages total).

* cited by examiner

Fig. 3

| No | File Name | Registration Date & Time | Analyzer | Device Name | Sample Name | | Data ID |
|---|---|---|---|---|---|---|---|
| 1 | related-4_013.lcd | 2015/09/17 2:36:48 | operator | Inst01 | A | | a00001 |
| 2 | related-4_012.lcd | 2015/09/17 1:06:04 | operator | Inst01 | B | | a00002 |
| 3 | related-4_011.lcd | 2015/09/17 0:47:29 | operator | Inst01 | C | | a00003 |
| 4 | related-4_010.lcd | 2015/09/16 0:04:31 | operator | Inst01 | D | | a00004 |
| 5 | related-4_009.lcd | 2015/09/16 23:15:10 | operator | Inst01 | E | | a00005 |
| 6 | related-4_008.lcd | 2015/09/16 22:37:15 | operator | Inst01 | F | | a00006 |
| 7 | related-4_007.lcd | 2015/09/16 21:48:21 | operator | Inst01 | G | | a00007 |
| 8 | related-4_006.lcd | 2015/09/16 20:56:06 | operator | Inst01 | H | | a00008 |
| 9 | related-4_005.lcd | 2015/09/16 20:04:31 | operator | Inst01 | I | | a00009 |
| 10 | related-4_004.lcd | 2015/09/16 19:13:57 | operator | Inst01 | J | | a00010 |
| 11 | related-4_003.lcd | 2015/09/16 18:11:03 | operator | Inst01 | K | | a00011 |
| 12 | related-4_002.lcd | 2015/09/16 17:09:40 | operator | Inst01 | L | | a00012 |
| 13 | related-4_001.lcd | 2015/09/16 16:07:41 | operator | Inst01 | M | | a00013 |

Audit Trail

| No | Category | Message | Sub-message | Date & Time | | User Name | Device Name |
|---|---|---|---|---|---|---|---|
| 1 | Login/Logout | User logged out. | | 2015/09/17 | 9:43:41 | operator | Inst01 |
| 2 | Information | Batch anaysis completed. | Demo_150916.lcb | 2015/09/17 | 3:06:34 | operator | Inst01 |
| 3 | File operation | File imported. | 2-104-1/_related-4_013.lcd | 2015/09/17 | 2:36:48 | operator | Inst01 |
| 4 | Information | Data collection started. | 2-104-1/_related-4_013.lcd | 2015/09/17 | 1:06:16 | operator | Inst01 |
| 5 | File operation | File imported. | 2-104-1/_related-4_012.lcd | 2015/09/17 | 1:06:04 | operator | Inst01 |
| 6 | Information | Data collection started. | 2-104-1/_related-4_012.lcd | 2015/09/16 | 23:35:44 | operator | Inst01 |
| ... | | | | | | | |
| 106 | File operation | File imported. | 2-104-1/_related-4_001.lcd | 2015/09/16 | 16:07:41 | operator | Inst01 |
| 107 | Information | Data collection started. | 2-104-1/_related-4_001.lcd | 2015/09/16 | 15:47:12 | operator | Inst01 |
| 108 | Information | Batch anaysis started. | Demo_150916.lcb | 2015/09/16 | 15:47:10 | operator | Inst01 |
| 109 | Audit trail | Device contents changed. | inst_Method.lcm | 2015/09/16 | 11:22:47 | operator | Inst01 |
| 110 | Login/Logout | User logged in. | | 2015/09/16 | 11:22:46 | operator | Inst01 |

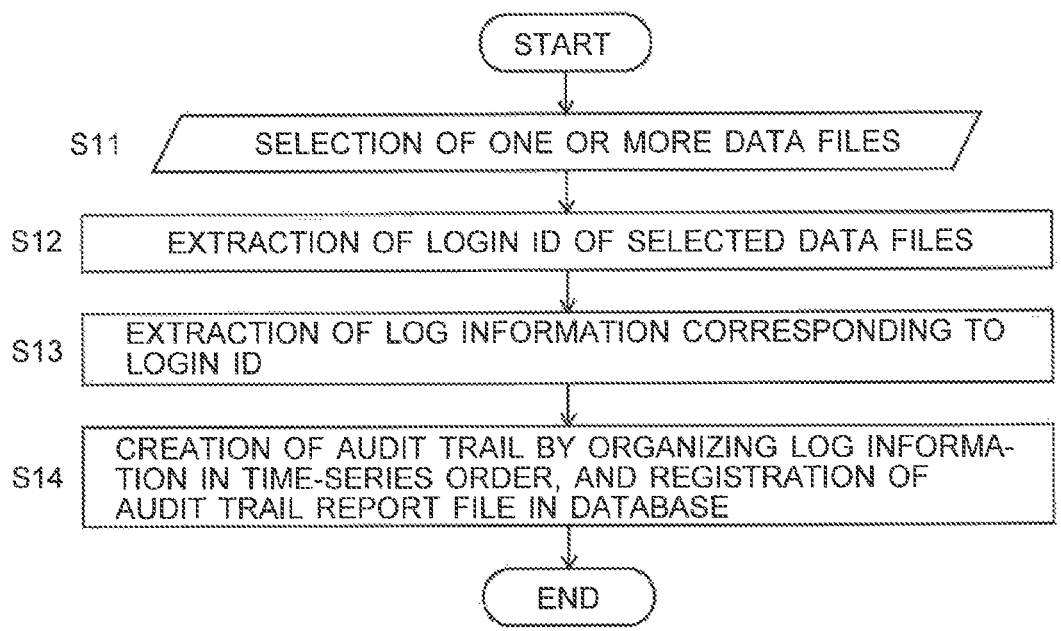

ANALYSIS INFORMATION MANAGEMENT SYSTEM

CROSS REFERENCE TO RELATED APPLICATIONS

This application is a National Stage of International Application No. PCT/JP2015/084498, filed Dec. 9, 2015.

TECHNICAL FIELD

The present invention relates to an analysis information management system for saving and managing information including data collected with various kinds of analytical instruments, such as a chromatograph apparatus, mass spectrometer or spectrophotometer. More specifically, it relates to a system for creating and managing an audit trail related to an analysis performed with such an analytical instrument.

BACKGROUND ART

In recent years, most of the tasks of processing and managing various data acquired with an analytical instrument, such as a gas chromatograph (GC), liquid chromatograph (LC) or mass spectrometer, have been performed by using a computer on which dedicated software was installed. In particular, a large-scale system in which multiple analytical instruments and computers (e.g. client terminals) as well as a database server and other devices are connected to each other through a communication network has also been proposed in recent years to meet various needs, such as the sophistication of analysis, automatic and efficient analyzing tasks, as well as the necessity for a centralized management of the measuring task and data-analyzing task (see Non-Patent Literature 1 and other documents). Typically, in such a system, the measurement data obtained for a sample in an analytical instrument, or process result data obtained by analytically processing the measurement data on a client terminal or the like, such as calculated values (e.g. quantitative values), are stored in a single data file for each sample. The data file is registered in, and managed on, a database constructed on a database server or similar location.

In recent years, such information management systems for analytical instruments have been required to completely comply with various regulations concerning electronic records and electronic signatures, such as "FDA 21 CFR Part 11" by the United States Food and Drug Administration (FDA) or the guidelines on electronic records and electronic signatures by the Japanese Ministry of Health, Labor and Welfare. To this end, all pieces of information concerning the login/logout operation by each user on each device (e.g. analytical instrument or computer) in the system as well as various operations related to each file are also registered as operation log information in the database, as described in Non-Patent Literature 1 or 2, Patent Literature 1, or other documents. In addition to such information concerning user operations, other kinds of information are also exhaustively registered as log information in the database, such as the beginning time and ending time of an analysis performed in an automatic analysis as well as information concerning the state of a device, such as an error, abnormality or the like which occurred in an analysis or in a data-analyzing process.

When a test result based on one or more data files needs to be submitted for a new-drug application or similar purposes, the integrity of those data files must be guaranteed. To this end, it is necessary to prepare an audit trail showing all pieces of log information related to the data files, from the login to the logout of a measurement operator or data analysis operator concerned, and submit the audit trail in a printed form or show it to an auditor on a display screen. In a conventional process of preparing such an audit trail, the measurement operator or other individuals extract necessary information from various kinds of log information stored in a database, by visually checking the date and time of the measurement or data analysis concerned, name of the data file, name of the measurement operator, name of the data analysis operator and other related information.

In a large-scale system including many devices, a huge amount of log information is stored in the database, since all pieces of log information received from the devices are stored in the database. Furthermore, a number of measurement operators may respectively perform a number of measurements, or a single measurement operator may concurrently perform analyzing operations using multiple analytical instruments during the same period of time. Therefore, the content of the log information stored in the database is extremely complex. Due to those factors, the task of extracting all pieces of log information related to specific data files is considerably burdensome and time-consuming. Additionally, in recent years, there has been the case where an audit trail related to many data files obtained by individually analyzing a large number of samples needs to be prepared. For the preparation of such an audit trail, the task of extracting log information from the database will be even more cumbersome and time-consuming.

The purpose of the audit trail is to guarantee the integrity of a data file. However, since the pieces of information in the audit trail are extracted by manual operations, an incorrect selection or omission of information may possibly occur. Therefore, the conventional method described above is not always suitable for the intended purpose, i.e. to guarantee the integrity. A searching or similar function normally included in database management software products may be used for extracting the necessary log information. However, since the conditions for such a search need to be manually entered by users, the possibility of an incorrect operation or intentional manipulation cannot be excluded. Accordingly, it is difficult to guarantee the integrity of the data file.

CITATION LIST

Patent Literature

Patent Literature 1: JP 2005-156473 A

Non Patent Literature

Non-Patent Literature 1: "CLASS-Agent Ver. 2 Nettowaaku Taiou Bunseki Deeta Kanri Tsuuru (Class-Agent Ver. 2, Network-Compatible Analysis Data Management Tool)", [online], Shimadzu Corporation, [accessed on Dec. 4, 2017], the Internet Non-Patent Literature 2: "FDA 21 CFR Part 11 Taiou Sofutouea WingSALD bio (WingSALD bio: A software in compliance with FDA 21 CFR Part 11)", [online], Shimadzu Corporation, [accessed on Dec. 4, 2017], the Internet

SUMMARY OF INVENTION

Technical Problem

The present invention has been developed to solve the previously described problem, and its objective is to provide an analysis information management system capable of efficiently creating an audit trail related to one or more data files which contain data obtained through a measurement, data obtained through a data-analyzing process or other relevant data, without leaving any room for human errors, artificial alterations or other unfavorable factors to be included in the process of creating the audit trail, so that a sufficiently reliable audit trail for guaranteeing the integrity of the data files will be obtained.

Solution to Problem

An analysis information management system according to the first aspect of the present invention developed for solving the previously described problem is an analysis information management system including a communication network, an analytical instrument connected to the communication network via a computer, a database server connected to the communication network, and a client terminal connected to the communication network, the analysis information management system configured to register, in a database constructed on the database server, a data file containing data acquired by performing an analysis on a sample with the analytical instrument and/or data acquired by performing a data-analyzing process using the client terminal, and to register various items of log information in the database, the items of log information including various operations on the computer and the client terminal as well as information showing a device state of the analytical instrument, in which:

the client terminal includes:
a) a file selector for allowing a user to select one or more data files for which an audit trail is to be created among data files registered in the database;
b) an audit trail information extractor for acquiring specific items of information contained in or associated with the one or more data files selected by the file selector, and for extracting, from the various items of log information, pieces of log information included within a period of time from a login to a logout related to the one or more data files, using the specific items of information as extraction keys, where the specific items of information minimally includes an identifier which identifies an analytical instrument and/or a computer used for acquiring data contained in the one or more data files, an identifier which identifies a user in charge of the task of acquiring the data, as well as information of the date and time of the creation of the one or more data files or the registration of the one or more data files in the database; and
c) an audit trail creator for creating an audit trail for the one or more data files by organizing the pieces of log information, extracted by the audit trail information extractor, in time-series order.

An analysis information management system according to the second aspect of the present invention developed for solving the previously described problem is an analysis information management system including a communication network, an analytical instrument connected to the communication network via a computer, a database server connected to the communication network, and a client terminal connected to the communication network, the analysis information management system configured to register, in a database constructed on the database server, a data file containing data acquired by performing an analysis on a sample with the analytical instrument and/or data acquired by performing a data-analyzing process using the client terminal, and to register various items of log information in the database, the items of log information including various operations on the computer and the client terminal as well as information showing a device state of the analytical instrument, in which:

the database server is configured to (i) save a login identifier as a part of the log information or in association with the log information when registering the log information in the database, the login identifier issued to identify each login every time an operation for logging into the computer or the client terminal is performed by a user, and to (ii) save the login identifier under which data to be stored in the one or more data files are acquired, in the one or more data files or in association with the one or more data files, when registering the one or more data files in the database; and the client terminal includes:
a) a file selector for allowing a user to select one or more data files for which an audit trail is to be created among data files registered in the database;
b) an audit trail information extractor for obtaining the login identifier contained in or associated with the one or more data files selected by the file selector, and for extracting, from the various items of log information, pieces of log information included within a period of time from a login to a logout related to the one or more data files, using the login identifier as an extraction key; and
c) an audit trail creator for creating an audit trail for the one or more data files by organizing the pieces of log information, extracted by the audit trail information extractor, in time-series order.

In the analysis information management system according to the present invention, the system may include a plurality of analytical instruments and a plurality of client terminals, and the database server and one of the client terminals (or the sole client terminal when the system includes a single client terminal) may be located on a single hardware unit. In other words, a computer serving as the client terminal may be configured to additionally function as the database server. The analytical instrument (or instruments) may be any type of device as long as it can perform an analysis and acquire a certain kind of data. The analytical instrument itself may be configured to effectively have the function of the computer and be directly connected to the communication network.

In the analysis information management system according to the first aspect of the present invention, a user who needs to prepare an audit trail related to one or more data files should perform a predetermined operation on the client terminal. In response to the operation, the file selector creates a list of property information including the file names of some of the data files registered in the database, and displays the list on the screen of a display unit. The file selector recognizes that the one or more data files specified by the user in the list have been selected.

The audit trail information extractor obtains specific items of information contained in the one or more data files selected in the previously described manner, or associated with those data files. The specific items of information include the identifier (ID) which identifies an analytical instrument or client terminal used for acquiring the data stored in those data files, an identifier which identifies the user who performed the task of acquiring those data, information of the date and time at which each data file was created, an identifier which identifies the data file, and other pieces of information. Any of those items of information can be given to each data file at the point in time where the data file is created or where the file is registered in the database. Using those items of information as the extraction key, the audit trail information extractor extracts, from the various items of log information registered in the database, all pieces of log information included within the period of time from the login to the logout related to the selected data files.

Specifically, for example, the audit trail information extractor can narrow down the log information based on the instrument identifier and the user identifier, and then extract, from the narrowed log information, the pieces of log information which were collected during the period of time from the login to the logout including the date and time of the creation or registration of the data files. The audit trail information extractor may preferably be configured to further obtain an identifier of each of the one or more data files selected by the file selector, the identifier contained in or associated with each individual data file, and to adopt, as a part of the pieces of log information included within the period of time from the login to the logout related to the one or more data files, the log information extracted from the various items of log information using the identifier as an extraction key.

The audit trail creator creates an audit trail for the one or more selected data files by sorting the pieces of log information, extracted in the previously described manner, in time-series order. As one mode of the present invention, the audit trail creator may create a report of the audit trail which lists the pieces of log information in a predetermined form, and register the report in the database as a file in PDF format (portable document format).

On the other hand, in the analysis information management system according to the second aspect of the present invention, the login identifier, which is issued every time an operation for logging into the computer provided for the analytical instrument or the client terminal is performed by a user, is used for the extraction of the log information. The login identifier is newly issued at every login of a user who has been logged out. Therefore, the login identifier can be used as information for identifying the period of time from the login to the logout of a user.

In the analysis information management system according to the second aspect of the present invention, when a piece of log information is to be registered in the database on the database server, or when a data file is to be registered in the database, the login identifier is saved in association with that log information or data file, or along with that log information or data file. When one or more data files are selected on the client terminal, the audit trail information extractor obtains the login identifier associated with those data files and extracts, from the various items of log information registered in the database, all pieces of log information related to the one or more data files, using the login identifier as the extraction key. Since each piece of log information is given a login identifier, the necessary pieces of log information can be easily extracted by conducting a search using the login identifier as a search key. As in the first aspect of the present invention, the audit trail creator creates an audit trail for the one or more selected data files by sorting the extracted pieces of log information in time-series order.

Advantageous Effects of Invention

With an analysis information management system according to the present invention, users only need to select one or more data files for which an audit trail needs to be created. The system automatically creates the audit trail related to those data files and registers it, for example, as a PDF file in the database. Users do not need to perform any cumbersome operation to search a huge amount of log information for the pieces of log information related to the target data files. The system can also prevent a deficiency or excess of log information due to an incorrect operation by a user as well as an artificial choice of log information, thereby enabling efficient preparation of a highly reliable audit trail suitable for guaranteeing the integrity of the data files.

BRIEF DESCRIPTION OF DRAWINGS

FIG. 3 is a schematic diagram showing a data file selection window for the process of creating an audit trail for data files.

FIG. 4 is a diagram showing one example of an audit trail report created through the process of creating an audit trail for data files.

FIG. 6 is a flowchart showing a process of creating an audit trail for data files in the analysis information management system according to the second embodiment.

DESCRIPTION OF EMBODIMENTS

First Embodiment

The first embodiment of the analysis information management system according to the present invention is hereinafter described with reference to the attached drawings.

Figure 1:
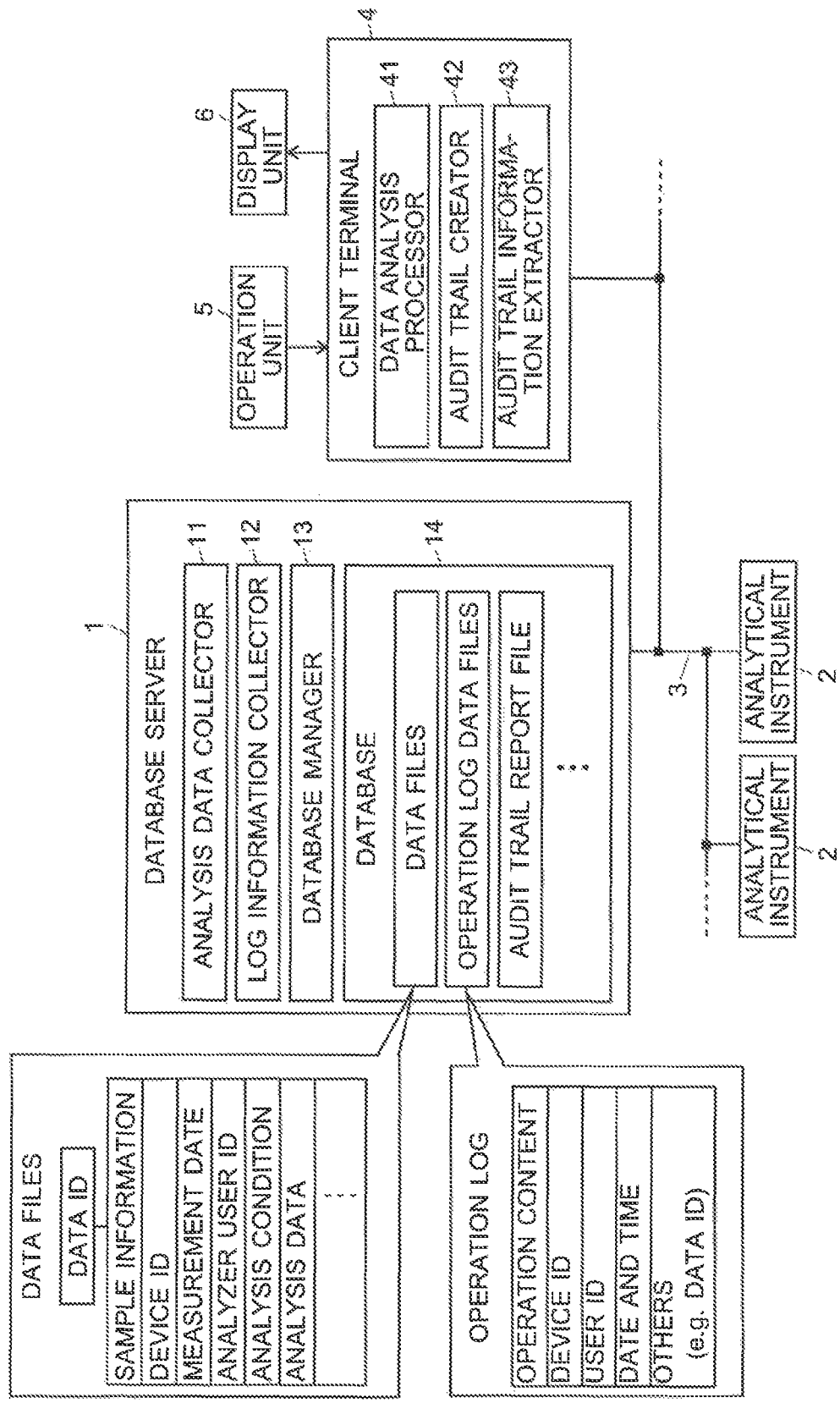
FIG. 1 is a schematic configuration diagram of the first embodiment of the analysis information management system according to the present invention.

FIG. 1 is a schematic configuration diagram of the main components of the analysis information management system according to the present embodiment.

The analysis information management system according to the first embodiment includes: one or more analytical instruments 2 for performing a predetermined analysis on a sample and collecting measurement data; a database server 1 which is actually a computer; and a client terminal 4 which is actually a personal computer. These three kinds of devices are connected to each other through a communication network 3, such as a local area network (LAN). An operation unit 5, which includes a mouse, keyboard and other devices, as well as a display unit 6, which is a monitor, are connected to the client terminal 4. Normally, an operation unit, display unit and other devices are also connected to the database server 1, although those units are not shown in FIG. 1.

Although the configuration shown in FIG. 1 has a single client terminal 4, there may be multiple client terminals. The client terminal 4 may additionally function as the database server 1. Each analytical instrument 2 may have built-in functions which effectively work similar to a computer and enable direct connection to the communication network 3. However, more typically, the analytical instrument is connected to the communication network 3 via a personal computer (not shown). In that case, two or more analytical instruments 2 may be connected to a single personal computer which is connected to the communication network 3. Such a personal computer may be configured to serve as a client terminal 4. The type of analytical instruments 2 is not specifically limited. Different types of analytical instruments may be connected to the communication network 3. For convenience of description, it is hereinafter assumed that the analytical instruments 2 are all liquid chromatograph (LC) apparatuses.

The database server 1 includes an analysis data collector 11, log information collector 12, database manager 13, database 14 and other functional blocks. The database 14 is used to store various kinds of data (files), although only the data files and operation log data files are specifically described in FIG. 1 to show their contents. The client terminal 4 includes a data analysis processor 41, audit trail creator 42, audit trail information extractor 43 and other functional blocks. As noted earlier, the database server 1 and the client terminal 4 are actually computers. Therefore, the aforementioned functional blocks are embodied by dedicated programs which are previously installed on those computers and executed on the same computers.

In the database server 1, the analysis data collector 11 collects data acquired in each analytical instrument 2 by an LC analysis on a sample as well as various items of information related to the analysis through the communication network 3. The collected data and information are registered through the database manager 13 in the database 14 as a data file. A data file normally contains various items of data and information related to an analysis on one sample. For example, as described in FIG. 1, those items of data and information include: sample information, such as the name and amount of the sample; device ID for identifying an analytical instrument used for the analysis; date and time of the analysis; analyzer user ID for identifying an individual who carried out the analysis; analysis conditions applied in the analysis (e.g. the flow velocity of the mobile phase); and analysis data acquired through the analysis. The same data file may additionally be used to store various kinds of calculated values obtained through a data-analyzing process based on the analysis data as well as other related items of information. For example, those additional values and information may specifically include: the conditions of the data-analyzing process (e.g. the condition of the waveform processing for peak detection); date and time of the execution of the data-analyzing process; data-analyzer user ID for identifying an individual who carried out the data-analyzing process; and calibration curve to be used for the quantitative calculation.

For each data file to be stored in the database 14, a data ID is automatically issued to identify the data file. This data ID is automatically issued when the data file is created or registered for the first time. An alteration of the data ID by users is basically prohibited.

The log information collector 12 collects various items of information through the communication network 3 and registers the information through the database manager 13 in the database 14 as the log information, such as an operation log data file. The items of information include operations and tasks performed by users on all analytical instruments 2, client terminal 4 and other devices included in the present system, as well as information indicating the state of each device, such as an error which occurred in an analytical instrument 2, client terminal 4 or other devices during an execution of a measurement or data-analyzing process. Typically, the operation log data file contains various kinds of data and information related to each specific operation. For example, as described in FIG. 1, the various kinds of data and information include: content of the operation; device ID for identifying an analytical instrument 2 or client terminal 4 on which the operation was performed; date and time of the operation; and user ID for identifying an operator who performed the operation. Other kinds of information may also be added; for example, if an operation related to the data file, such as saving, reading or printing the file, has been performed, the data ID which identifies the data file on which the operation was performed is added to the operation log data file.

Subsequently, an audit trail creation process, which is a characteristic operation in the analysis information management system according to the present invention, is described. This process is performed when an audit trail related to a data file needs to be created in order to substantiate the integrity of the content of the data file.

Figure 2:
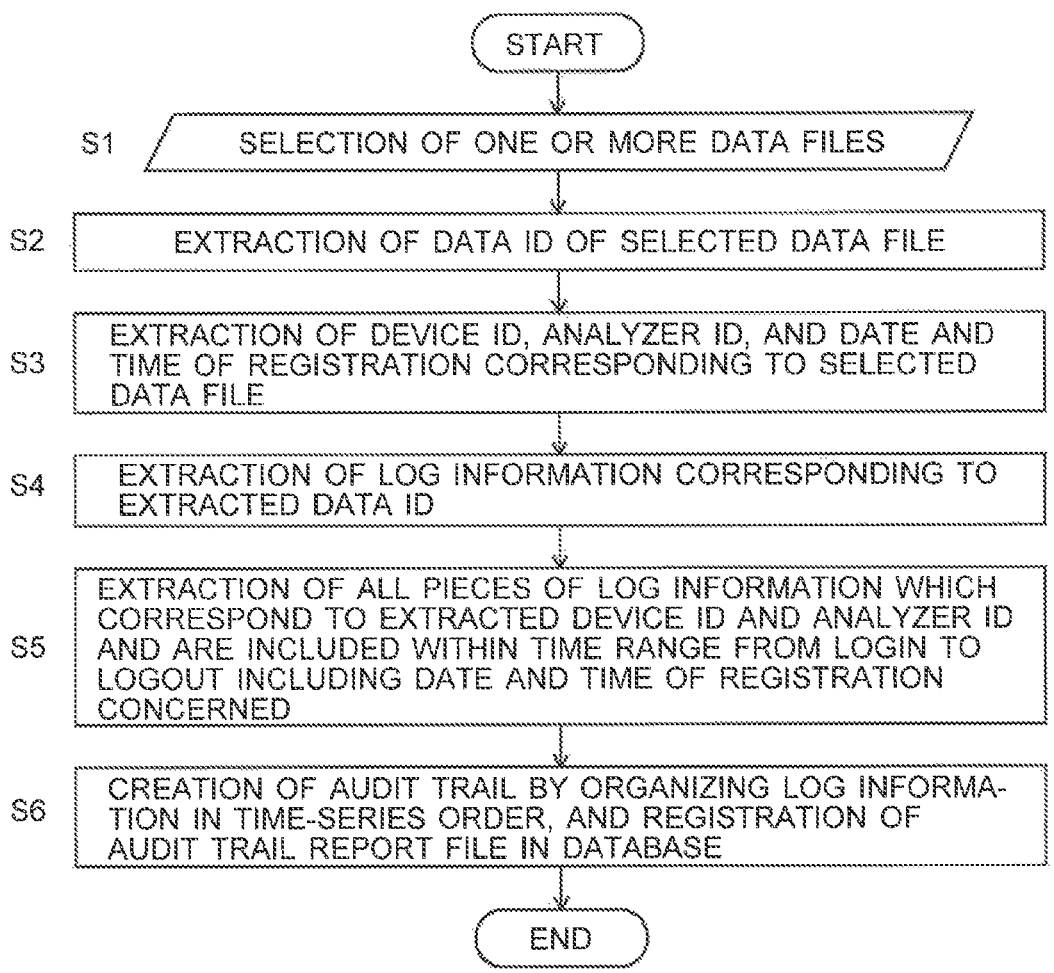
FIG. 2 is a flowchart showing a process of creating an audit trail for data files in the analysis information management system according to the first embodiment.

FIG. 2 is a flowchart showing the process of creating an audit trail for data files in the analysis information management system according to the present embodiment.

A user (who is hereinafter called the "operator") who needs to prepare an audit trail performs a predetermined operation using the operation unit 5 of the client terminal 4, whereupon the audit trail creator 42 begins to operate and display an audit trail creation window on the screen of the display unit 6. In this audit trail creation window, a list of data files which satisfy specific narrowing conditions among the data files registered in the database 14 can be displayed. On this list, the operator selects one or more data files for which the audit trail needs to be created (Step S1).

In an LC analysis or the like, an LC apparatus is often used which performs an analysis on each sample while sequentially replacing one sample with another using an autosampler in which many samples can be loaded beforehand. In an analysis using such an analytical instrument 2, it is often the case that a plurality of samples which form one group are collectively evaluated from the result of a data-analyzing process based on a plurality of sets of analysis data respectively acquired for those samples. Accordingly, the analysis information management system according to the present invention is configured so that a plurality of samples can be previously registered as a batch, and the data files corresponding to the samples included in the batch can be constantly handled as a bundle of data files. The batch can be set before the execution of an analysis, or it may be set after the completion of the analysis. In such a case, the operator can select one batch as the target for which the audit trail should be created, whereby a plurality of data files corresponding to the samples included in the batch are simultaneously selected as the target for which the audit trail should be created.

FIG. 3 is a schematic diagram showing a data file selection window for the process of creating an audit trail for data files. This example shows the result of a search for the data files whose file names include the character string "related-4". A total of 13 data files are shown in the data-file list 100. It is hereinafter assumed that all 13 data files have been selected as the target for which the audit trail should be created. It should be noted that a list 101 of data IDs corresponding to the respective data files is shown on the right side of the data file list 100 in FIG. 3. The list 101 is not one which will be actually displayed on the screen, but is merely shown on the drawing for convenience of explanation.

After selecting one or more data files, the operator issues a command to create an audit trail. Upon receiving this command, the audit trail information extractor 43 extracts data IDs which respectively correspond to the selected data files (Step S2). In the example of FIG. 3, the data ID "a00001" is extracted for the data file with the file name "_related-4_013.1cd". As already explained, the data ID is the identifier of the data file. The audit trail information extractor 43 also extracts the device ID, analyzer user ID as well as the date and time of registration corresponding to the selected data files (Step S3). These items of information are all contained in the individual data files or saved in association with those data files.

Next, the audit trail information extractor 43 accesses the database 14 through the communication network 3, and searches for and extracts operation log data files as well as other pieces of information in which any of the data IDs extracted in Step S2 is contained (Step S4). Simultaneously with this search, before or after that, the audit trail information extractor 43 initially extracts operation log data files and other pieces of information corresponding to the device ID and user ID extracted in Step S3, and further searches the extracted information for the operation log data files and other pieces of log information which correspond to the time range from the login to the logout including the date and time of registration (Step S5).

For example, an operation log data file which records operations directly related to data files, such as the saving or reading of a data file, contains a data ID. Such operation logs can be extracted by a search using the data ID as a search key. However, for example, logs which show operations that are not directly related to data files cannot be extracted by a search using the data ID as a search key. Examples of such logs include those related to a login operation, logout operation, or task of changing analysis conditions in an analytical instrument 2, as well as those which show the state of an analytical instrument 2, such as the initiation of a measurement or the completion of the measurement. Such types of log information which are not directly related to data files can also be extracted by the process in Step S5 without omission.

The audit trail creator 42 creates an audit trail in a predetermined format by organizing the various items of log information, extracted by the audit trail information extractor 43 as just described, in time-series order (Step S6). FIG. 4 is a diagram showing one example of an audit trail report 110 created through the process of creating an audit trail for data files. In this example, the audit trail report 110 is created in the form of a list in which one of the prepared messages is selected according to the content of each log information, along with the file name of the data file and other items of information as the sub-message. The date-and-time information, the type of user concerned, and other pieces of information are also listed. The audit trail report created in this manner is transmitted as an electronic file in PDF format to the database server 1 and registered in the database 14. It is naturally possible to create a hard copy of the completed audit trail report through a printer (not shown) in response to an operation by an operator or other individuals.

Thus, the analysis information management system according to the present embodiment can automatically create an audit trail containing all pieces of log information related to one or more data files selected by an operator.

As noted in the previous description, a data file which contains data acquired through an analysis may be used to contain additional information, such as the data obtained through a data-analyzing process. The system can also be configured to similarly handle calculation result data files which contain data obtained through a data-analyzing process, such as the result of a quantitative analysis, but does not contain sample analysis data, i.e. to automatically create an audit trail related to one or more calculation result data files when those files are selected by a user.

Second Embodiment

Figure 5:
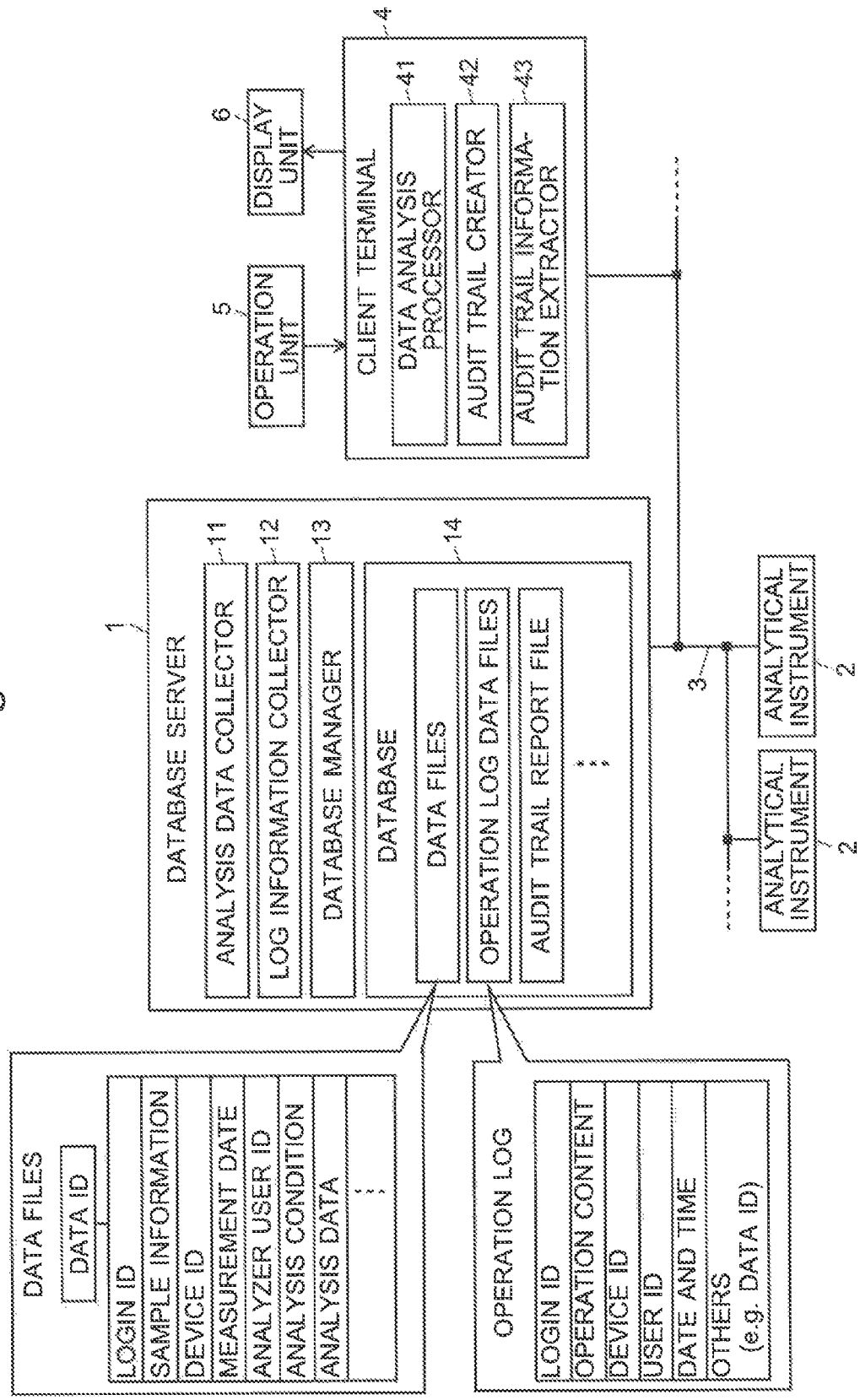
FIG. 5 is a schematic configuration diagram of the second embodiment of the analysis information management system according to the present invention.

The second embodiment of the analysis information management system according to the present invention is hereinafter described with reference to the attached drawings. FIG. 5 is a schematic configuration diagram of the analysis information management system according to the second embodiment. FIG. 6 is a flowchart showing the process of creating an audit trail for data files in the analysis information management system according to the second embodiment. In FIG. 5, the components which are identical or correspond to those in the first embodiment are denoted by the same reference signs. Only the differences from the analysis information management system according to the first embodiment will be hereinafter described in detail.

In the analysis information management system according to the second embodiment, a login ID for uniquely identifying each login is issued every time a user logs into any of the computers included in the system, i.e. the personal computers provided for the analytical instruments 2, the client terminal 4 and the database server 1. When registering a piece of log information which includes all operations performed within the period of time from the login to the logout as well as the information that occurred in any analytical instrument 2 or other devices within that period of time (i.e. error information), the log information collector 12 saves the login ID along with the log information in the database 14. On the other hand, when registering analysis data acquired with an analytical instrument 2 as an analysis data file in the database 14, the analysis data collector 11 obtains the login ID under which the data were acquired, and saves this login ID along with the data.

When a plurality of data files containing data that were acquired with one analytical instrument 2 while an operator was logged into the personal computer provided for that analytical instrument 2 are registered in the database 14, those data files will be associated with the same login ID. This means that the login ID can be used as information for identifying the login under which a data file was created. Accordingly, in the analysis information management system according to the present embodiment, a search using the login ID as a search key is conducted to extract log information related to the data files.

That is to say, as in the first embodiment, after selecting one or more data files, the operator issues a command to create an audit trail (Step S11). Upon receiving this command, the audit trail information extractor 43 extracts the login ID which corresponds to the selected data files (Step S12). Subsequently, the audit trail information extractor 43 accesses the database 14 through the communication network 3, and searches for and extracts operation log data files as well as other pieces of log information to which the login ID extracted in Step S12 is given (Step S13). Since all pieces of log information are respectively given login IDs, it is possible to extract all pieces of log information related to the target data files by a search using the login ID as a search key.

The audit trail creator 42 creates an audit trail in a predetermined format by organizing the pieces of log information, extracted by the audit trail information extractor 43 as just described, in time-series order, and registers the audit trail report in the database 14 as an electronic file in PDF format, for example (Step S14).

Thus, in the analysis information management system according to the second embodiment, a login ID is issued to every login operation by a user, and this login ID is used for the creation of the audit trail to easily and quickly extract log information necessary for creating an audit trail.

It should be noted that the previous embodiments are mere examples of the present invention, and any modification, addition or change appropriately made within the spirit of the present invention will evidently fall within the scope of claims of the present application.

REFERENCE SIGNS LIST

1 . . . Database Server
11 . . . Analysis Data Collector
12 . . . Log Information Collector
13 . . . Database Manager
14 . . . Database
2 . . . Analytical Instrument
3 . . . Communication Network
4 . . . Client Terminal
41 . . . Data Analysis Processor
42 . . . Audit Trail Creator
43 . . . Audit Trail Information Extractor
5 . . . Operation Unit
6 . . . Display Unit

The invention claimed is:

1. An analysis information management system comprising:
a communication network;
an analytical instrument connected to the communication network via a computer;
a database server connected to the communication network, the database server including a database; and
a client terminal connected to the communication network,
wherein the database is configured to register (i) a plurality of data files including at least one of data acquired by performing an analysis on a sample with the analytical instrument and data acquired by performing a data-analyzing process using the client terminal, and (ii) items of log information including operations on the computer and the client terminal and information of a device state of the analytical instrument, and
wherein the client terminal comprises:
a) a file selector configured to select, based on an input by a user, an audit trail creation target by selecting one or more data files among the plurality of data files registered in the database;
b) an audit trail information extractor configured to acquire specific items of information associated with the one or more data files selected by the file selector, and extract, from the items of log information, pieces of log information included within a period of time from a login time to a logout time related to the one or more data files, using the specific items of information as extraction keys, where the specific items of information includes a first identifier that identifies at least one of the analytical instrument and the computer used for acquiring data contained in the one or more data files, and a second identifier that identifies the user in charge of a task of acquiring the data and information of date and time of creation or registration of the one or more data files in the database; and
c) an audit trail creator configured to create an audit trail of the audit trail creation target by organizing the pieces of log information, extracted by the audit trail information extractor, in time-series order.

2. The analysis information management system according to claim 1, wherein:
the audit trail information extractor is further configured to obtain a third identifier of each of the one or more data files selected by the file selector, the third identifier associated with each individual data file, and to adopt, as a part of the pieces of log information included within the period of time from the login time to the logout time related to the one or more data files, the log information extracted from the items of log information using the third identifier as an extraction key.

3. An analysis information management system comprising:
a communication network;
an analytical instrument connected to the communication network via a computer;
a database server connected to the communication network, the database server including a database; and
a client terminal connected to the communication network,
wherein the database is configured to register (i) a plurality of data files including at least one of data acquired by performing an analysis on a sample with the analytical instrument and data acquired by performing a data-analyzing process using the client terminal, and (ii) items of log information including operations on the computer and the client terminal and information of a device state of the analytical instrument,
wherein the client terminal comprises:
a) a file selector configured to select, based on an input by the user, an audit trail creation target by selecting one or more data files among the plurality of data files registered in the database;
b) an audit trail information extractor configured to obtain a login identifier associated with the one or more data files selected by the file selector, and extract, from the items of log information, pieces of log information included within a period of time from a login time to a logout time related to the one or more data files, using the login identifier as an extraction key; and
c) an audit trail creator configured to create an audit trail of the audit trail creation target by organizing the pieces of log information, extracted by the audit trail information extractor, in time-series order, and
wherein the database server is configured to (i) save the login identifier as a part of the log information or in association with the log information when registering the log information in the database, the login identifier identifying each login every time an operation for logging into the computer or the client terminal is performed by a user, and to (ii) save the login identifier under which data to be stored in the one or more data files are acquired, in the one or more data files or in association with the one or more data files, when registering the one or more data files in the database.

4. The analysis information management system according to claim 1, wherein:
the audit trail creator is further configured to create a report of the audit trail which lists the pieces of log information in a predetermined form, and register the report in the database as a file in PDF format.

5. The analysis information management system according to claim 2, wherein:
the audit trail creator is further configured to create a report of the audit trail which lists the pieces of log information in a predetermined form, and register the report in the database as a file in PDF format.

6. The analysis information management system according to claim 3, wherein:
the audit trail creator is further configured to create a report of the audit trail which lists the pieces of log information in a predetermined form, and register the report in the database as a file in PDF format.

* * * * *